(12) United States Patent
Brahmachari et al.

(10) Patent No.: US 6,623,927 B1
(45) Date of Patent: Sep. 23, 2003

(54) METHOD OF DETECTION OF ALLELIC VARIANTS OF SCA2 GENE

(75) Inventors: Samir Kumar Brahmachari, Delhi (IN); Shweta Choudhry, Delhi (IN); Mitali Mukerji, Delhi (IN); Satish Jain, New Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/707,919

(22) Filed: Nov. 8, 2000

(51) Int. Cl.⁷ ............................ C07H 21/04; C12G 1/68

(52) U.S. Cl. ................ 435/6; 536/23.1; 536/24.3; 536/24.31; 435/91.2

(58) Field of Search ............................ 435/6; 536/23.1, 536/24.3, 24.31

(56) References Cited

PUBLICATIONS

Ahern. The Scientist, vol. 9, No. 15, p. 20, Jul. 1995.*
Pulst et al. "Moderate expansion of a normally biallelic trinucleotide repeat in SCA2" Nature Genetics, VOl 14, pp. 269–276, Nov. 1996.*
Muzny et al. Genbank Accession No. AC004085, Nov. 6, 2000.*
Imbert et al. Genbank Accession No. Y08262, Jan. 1997.*
Pulst et al. Genbank Accession No. U70323, Nov. 1996.*

* cited by examiner

Primary Examiner—Gary Benzion
Assistant Examiner—Jeanine Goldberg
(74) Attorney, Agent, or Firm—Venable LLP; Ann S. Hobbs

(57) ABSTRACT

The present invention relates to allelic variants of human Spinocerebellar ataxia 2 (SCA2) gene and provides allele-specific primers and probes suitable for detecting these allelic variants for applications such as molecular diagnosis, prediction of an individual's disease susceptibility, and/or the genetic analysis of SCA2 gene in a population.

4 Claims, 13 Drawing Sheets

SNP Details

SNP:
  Handle|local_snp_id:   FGU-CBT | SKB.2K.1.1
  NCBI Assay Id(ss#):    869704
  Reference SNP Id(rs#): 695871

STS Information: Not submitted

---

From SNP Database:
Submitter Handle:            FGU-CBT
Submitter Batch ID:          SKB.2K.1
Release Date:                Aug. 2 2000  2:53PM
Molecular type:              Genomic
No. of Chromosomes sampled:  215
Synonym defined:
Organism:                    Homo sapiens
Population:                  INDPOP
Submitter Method ID:         SCA2-SNP
Citation:
  Single Nucleotide Polymorphism in SCA2 Gene.

View citation details

---

NCBI Assay ID:       869704
Submitter SNP ID:    SKB.2K.1.1
Synonyms:
LOCUSID:             6311
Submitter STS ID:
STS Accession:       not available
GenBank Accession:   U70323
Gene Name:           Human ataxin-2 gene/ Spinocerebellar ataxia 2 (SCA2) gene
Length:              459

Flanking Sequence Information:

5'Assay: CTCCGCCTCA GACTGTTTTG GTAGCAACGG CAACGGCGGC GGCGCGTTTC GGCCCGGCTC
         CCGGCGGCTC CTTGGTCTCG GCGGGCCTCC CCGCCCCTTC GTCGTC (SEQ ID NO: 14)

Observed: G/C

3'Assay: TCCTTCTCCC CCTCGCCAGC CCGGGCGCCC CTCCGGCCGC GCCAACCCGC GCCTCCCCGC
         TCGGCGCCCG TGCGTCCCCG CCGCGTTCCG GCGTCTCCTT GGCGCGCGCT GCTCCCGGCT
         GTCCCCGCCC GGCGTGCGAG CCGGTGTATG GGCCCCTCAC CATGTCGCT (SEQ ID NO: 15)

3'Flank: GAAGCCCCAG CAGCAGCAGC AGCAGCAGCA GCAACAGCAG CAGCAGCAAC AGCAGCAGCA
         GCAGCAGCAG CAGCCGCCGC CCGCGGCTGC CAATGTCCGC AAGCCCGGCG GCAGCGGCCT
         TCTAGCGTCG CCCGCCGCCG CGCCTTCGCC GTCCTCGTCC TCGGTCTCCT CGTCCTCGGC
         CAC (SEQ ID NO: 16)

---

Allele Frequency Information:
  POP Batch Id: SKB.2K.1:
Submitter Handle:     FGU-CBT
Submitter Method ID:  SCA2-SNP
Citation:
  Single Nucleotide Polymorphism in SCA2 Gene.

Handle|PopulationID:       FGU-CBT| INDPOP
  No. of Chromosomes Sampled: 215

Allele: C = 0.293 / G = 0.707

*FIG 4A*

Reference SNP Record
NCBI SNP ID: rs695871

NCBI Resource Links

GenBank: U70323

LocusLink: no link established

Integrated Maps: *under construction*

Submitter records for this ID:

Assay ID    Handle | Local Submitter ID    Release Date ss869704    FGU-CBT|SKB.2K.1.1    Aug 2 2000 2:53PM

Variation Summary:

Assay sample size (number of chromosomes) : 430
Population data sample size (number of chromosomes) :
Total number of populations with frequency data: 1
Total number of individuals with genotype data: 0
Average estimated heterozygosity: 0.414
Average Allele Frequency:

C:        0.293
    G:        0.707

Validation Summary:

Marker displays Mendelian segregation: UNKNOWN
PCR results confirmed in multiple reactions: YES
Homozygotes detected in individual genotype data: UNKNOWN
Insufficient genotype data to compute the goodness of fit to Hardy-Weinberg
Insufficient data to compute individual x genotype consistency measures
Validation status: *under construction*

*FIG 4B*

Submitter Contact Details

This batch's contact information:

| | |
|---|---|
| handle: | FGU-CBT |
| name: | Shweta Choudhry |
| fax: | +91-11-7257471 |
| phone: | +91-11-7416489 |
| email: | shwetachoudhry@hotmail.com |
| lab: | Functional genomics Unit |
| institution: | Centre for Biochemical Technology (CSIR) |
| address: | Delhi University Campus, Mall Road, Delhi- 110007, India |

Handle information for the lab:

| | |
|---|---|
| handle: | FGU-CBT |
| name: | Prof. Samir K. Brahmachari |
| fax: | +91-11-7257471 |
| phone: | +91-11-7416489 |
| email: | skb@cbt.res.in |
| lab: | Functional genomics Unit |
| institution: | Centre for Biochemical Technology (CSIR) |
| address: | Delhi University Campus, Mall Road, Delhi- 110007, India |

*FIG. 4C*

SNP Population Details - 558

Submitter Population Handle: FGU-CBT
Submitter population ID: INDPOP
Population Text:

Continent: Asia
    Nation: India

View SNP used on this population

*FIG 4D*

SNP Method Details - 564

Submitter Method Handle: FGU-CBT
Submitter Method ID: SCA2-SNP
Method Text:
The region containing the SNP was PCR amplified using the
primers SCA2-FP3 (5' CTCCGCCTCAGACTGTTTTGGTAG 3') (SEQ ID NO: 1)
and SCA2-RP3 (5' GTGGCCGAGGACGAGGAGAC 3') (SEQ ID NO. 2).
Approximately 100ng of genomic DNA was amplified in a 50ml
reaction volume containing a final concentration of 5mM Tris,
25mM KCl, 0.7mM MgCl2, 0.05% gelatin, 20pmol of each primer and
0.5U of Taq DNA polymerase. Samples were denatured at 94oC for
3 min followed by 35 cycles of denaturation (94oC, 45sec),
annealing (52oC, 30sec), extension (72oC, 45sec) and a final
extension of 7 min at 72oC in a Perkin Elmer GeneAmp PCR System
9600. The PCR product was purified from band cut out of the
agarose gel using QIAquick gel extraction kit (Qiagen) and was
directly sequenced using dye terminator chemistry on an ABI
Prism 377 automated DNA sequencer with the PCR primers.

View SNP found using this method
View SNP with population data obtained with this method

*FIG. 4E*

SNP Publication Details

Submitter Handle: FGU-CBT
pmid:
MEDUID:
TITLE:
  Single Nucleotide Polymorphism in SCA2 Gene.
AUTHOR:
  CHOUDHRY, S.; BRAHMACHARI, S.K.
JOURNAL:          •
VOLUME:           •
SUPPL:            •
ISSUE:            •
I_SUPPL:          •
PAGES:            •
YEAR:             2000
STATUS:           1- unpulished Searched PubMed by Author:
CHOUDHRY, S.; BRAHMACHARI, S.K.
View SNP linked to this publication

*FIG. 4F*

SNP Details

SNP:
  Handle|local_snp_id:       FGU-CBT | SKB.2K.1.2
  NCBI Assay Id(ss #):       869705
  Reference SNP Id(rs #):    696872

STS Information: Not submitted

From SNP Database:
Submitter Handle:            FGU-CBT
Submitter Batch ID:          SKB.2K.1
Release Data:                Aug 2 2000  2:53PM
Molecular type:              Genomic
No. of Chromosomes sampled:  215
Synonym defined:
Organism:                    Homo sapiens
Population:                  INDPOP
Submitter Method ID:         SCA2-SNP
Citation:
   Single Nucleotide Polymorphism in SCA2 Gene.
View citation details

| | |
|---|---|
| NCBI Assay ID: | 869705 |
| Submitter SNP ID: | SKB.2K.1.2 |
| Synonyms: | |
| LOCUSID: | 6311 |
| Submitter STS ID: | |
| STS Accession: | not available |
| GenBanK Accession: | U70323 |
| Gene Name: | Human ataxin-2 gene/Sphinocerebellar ataxia 2 (SCA2) gene |
| Length: | 459 |

Flanking Sequence Information:

```
5'Assay: CTCCGCCTCA GACTGTTTTG GTAGCAACGG CAACGGCGGC GGCGCGTTTC GGCCCGGCTC
         CCGGCGGCTC CTTGGTCTCG GCGGGCCTCC CCGCCCCTTC GTCGTCGTCC TTCTCCCCCT
         CGCCAGCCCG GGCGCCCCTC CGGCCGCGCC AACCCGCGCC TCCCCGCTCG GCGCCCG
Observed: T/C                                              (SEQ ID NO.: 17)
3'Assay: GCGTCCCCGC CGCGTTCCGG CGTCTCCTTG GCGCGCCCGG CTCCCGGCTG TCCCCGCCCG
         GCGTGCGAGC CGGTGTATGG GCCCCTCACC ATGTCGCT            (SEQ ID NO.: 18)
3'Assay: GAAGCCCCAG CAGCAGCAGC AGCAGCAGCA GCAACAGCAG CAGCAGCAAC AGCAGCAGCA
         GCAGCAGCAG CAGCCGCCGC CCGCGGCTGC CAATGTCCGC AAGCCCGGCG GCAGCGGCCT
         TCTAGCGTCG CCCGCCGCCG CGCCTTCGCC GTCCTCGTCC TCGGTCTCCT CGTCCTCGGC
         CAC (SEQ ID NO.: 16)
```

Allele Frequency Information:
POP Batch Id: SKB.2K.1:
Submitter Handle:        FGU-CBT
Submitter Method ID:     SCA2-SMP
Citation:
   Single Nucleotide Polymorphism in SCA2 Gene.
   Handle| Population ID:    FGU-CBT | INDPOP
   No. of Chromosomes Sampled:   215
       Allele: C = 0.293 / T = 0.707

*FIG 5A*

Reference SNP Record

NCBI SNP ID: rs695872

NCBI Resource Links

GenBank: U70323

LocusLink: no link established

Integrated Maps: *under construction*

Submitter records for this ID:

| Assay ID | Handle \| Local Submitter ID | Release Date |
|---|---|---|
| ss869705 | FGU-CBT \| SKB.2K.1.2 | Aug 2 2000 2:53PM |

Variation Summary:

Assay sample size (number of chromosomes): 430
Population data sample size (number of chromosomes):
Total number of populations with frequency data: 1
Total number of individuals with genotype data: 0
Average estimated heterozygosity: 0.414
Average Allele Frequency:
    C: 0.293
    T: 0.707

Validation Summary:

Marker displays Mendelian segregation: UNKNOWN
PCR results confirmed in multiple reactions: YES
Homozygotes detected in individual genotype data: UNKNOWN
Insufficient genotype data to compute the goodness of fit to Hardy-Weinberg
Insufficient data to compute individual x genotype consistency measures
Validation status: *under construction*

*FIG. 5B*

SNP Publication Details

Submitter Handle:
pmid:
MEDUID:
TITLE:
    Single Nucleotide Polymorphism in SCA2 Gene.
AUTHOR:
    CHOUDHRY, S.; BRAHMACHARI, S. K.
JOURNAL: •
VOLUME: •
SUPPL: •
ISSUE: •
I_SUPPL: •
PAGES: •
YEAR:     2000
STATUS:     1- unpulished Searched PubMed by author:
CHOUDHRY S.: BRAHMACHARI, S.K.

View SNP linked to this publication

FIG. 5C

SNP Population Details - 558

Submitter Population Handle:   FCU-CBT
Submitter Population ID:   INDPOP
Population Text:

Continent: Asia
    Nation: India

View SNP used on this population

FIG 5D

SNP Method Details - 564

Submitter Method Handle:   FGU-CBT
Submitter Method ID:       SCA2-SNP
Method Text:
```
The region containing the SNP was PCR amplified using the
primers SCA2-FP3 (5' CTCCGCCTCAGACTGTTTTGGTAG 3')(SEQ ID NO: 1)
and SCA2-RP3 (5' GTGGCCGAGGACGAGGAGAC 3') (SEQ ID NO. 2).
Approximately 100ng of genomic DNA was amplified in a 50ml
reaction volume containing a final concentration of 5mM Tris,
25mM KCl, 0.7mM MgCl2, 0.05% gelatin, 20pmol of each primer and
0.5U of Taq DNA polymerase. Samples were denatured at 94oC for
3 min followed by 35 cycles of denaturation (94oC, 45sec),
annealing (52oC, 30sec), extension (72oC, 45sec) and a final
extension of 7 min at 72oC in a Perkin Elmer GeneAmp PCR System
9600. The PCR product was purified from band cut out of the
agarose gel using QIAquick gel extraction kit (Qiagen) and was
directly sequenced using dye terminator chemistry on an ABI
Prism 377 automated DNA sequencer with the PCR primers.
```
View SNP found using this method
View SNP with population data obtained with this method

*FIG. 5E*

Submitter Contact Details

This batch's contact information:
| | |
|---|---|
| handle: | FGU-CBT |
| name: | Shweta Choudhry |
| fax: | +91-11-7257471 |
| phone: | +91-11-7416489 |
| email: | shwetachoudhry@hotmail.com |
| lab: | Functional genomics Unit |
| institution: | Centre for Biochemical Technology (CSIR) |
| address: | Delhi University Campus, Mall Road, Delhi- 110007, India |

Handle information for the lab:
| | |
|---|---|
| handle: | FGU-CBT |
| name: | Prof. Samir K. Brahmachari |
| fax: | +91-11-7257471 |
| phone: | +91-11-7416489 |
| email: | skb@cbt.res.in |
| lab: | Functional genomics Unit |
| institution: | Centre for Biochemical Technology (CSIR) |
| address: | Delhi University Campus, Mall Road, Delhi- 110007, India |

*FIG 5F*

```
LOCUS       HSU70323                4481 bp    mRNA            PRI 20-NOV-1996
DEFINITION  Human ataxin-2 (SCA2) mRNA, complete cds.
ACCESSION   U70323
VERSION     U70323.1  GI:1679683
KEYWORDS    
SOURCE      human.
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 4481)
  AUTHORS   Pulst,S.-M., Nechiporuk,A., Nechiporuk,T., Gispert,S., Chen,X.-N.,
            Lopes-Cendes,I., Pearlman,S., Starkman,S., Orozco-Diaz,G.,
            Lunkes,A., DeJong,P., Rouleau,G.A., Auburger,G., Korenberg,J.R.,
            Figueroa,C. and Sahba,S.
  TITLE     Moderate expansion of a normally biallelic trinucleotide repeat in
            spinocerebellar ataxia type 2
  JOURNAL   Nat. Genet. 14 (3), 269-276 (1996)
  MEDLINE   97051920
REFERENCE   2  (bases 1 to 4481)
  AUTHORS   Pulst,S.-M.
  TITLE     Direct Submission
  JOURNAL   Submitted (10-SEP-1996) Medicine, Cedars-Sinai, 8700 Beverly Blvd.,
            Los Angeles, CA 90048, USA
FEATURES         Location Qualifiers
     source      1..4481
                 /organism="Homo sapiens"
                 /db_xref="taxon:9606"
                 /chromosome="12"
                 /map="12q24.1"
     gene        163..4101
                 /gene="SCA2"
     CDS         163..4101
                 /gene="SCA2"
                 /standard_name="spinocerebellar ataxia type 2"
                 /codon_start=1
                 /product="ataxin-2"
                 /protein_id="AAV19200.1"
                 /db_xref="GI:1679684"
                 /translation="MRSAAAAPRSPAVATESRRFAAARWPGWRSLQRPARRSGRGGGG
                 AAPGPYPSAAPPPPGPGPPPSRQSSPPSASDCFGSNGNGGGAFRPGSRRLLGLGGPPR
                 PFVVVLLPLASPGAPPAAPTRASPLGARASPPRSGVSLARPAPGCPRPACEPVYGPLT
                 MSLKPQQQQQQQQQQQQQQQQQQQQQQQPPPAAANVRKPGGSGLLASPAAAPSPSSSSV
                 SSSSATAPSSVVAATSGGGRPGLGRGRNSNKGLPQSTISFDGIYANMRMVHILTSVVG
                 SKCEVQVKNGGIYEGVFKTYSPKCDLVLDAAHEKSTESSSGPKREEIMESILFKCSDF
                 VVVQFKDMDSSYAKRDAPTDSAISAKVNGEHKEKDLEPWDAGELTANEELEALENDVS
                 NGWDPNDMFRYNEENYGVVSTYDSSLSSYTVPLERDNSEEFLKREARANQLAEEIESS
                 AQYKARVALENDDRSEEEKYTAVQRNSSEREGHSINTRENKYIPPGQRNREVISWGSG
                 RQNSPRMGQPGSGSMPSRSTSHTSDFNPNSGSDQRVVNGGVPWPSPCPSPSSRPPSRY
                 QSGPNSLPPRAATPTRPPSRPPSRPSRPPSHPSAHGSPAPVSTMPKRMSSEGPPRMSP
                 KAQRHPRNHRVSAGRGSISSGLEFVSHNPPSEAATPPVARTSPSGGTWSSVVSGVPRL
                 SPKTHRPRSPRQNSIGNTPSGPVLASPQAGIIPTEAVAMPIPAASPTPASPASNRAVT
                 PSSEAKDSRLQDQRQNSPAGNKENIKPNETSPSFSKAENKGISPVVSEHRKQIDDLKK
                 FKNDFRLQPSSTSESMDQLLNKNREGEKSRDLIKDKIEPSAKDSFIENSSSNCTSGSS
                 KPNSPSISPSILSNTEHKRGPEVTSQGVQTSSPACKQEKDDKEEKKDAAEQVRKSTLN
                 PNAKEFNPRSFSQPKPSTTPTSPRPQAQPSPSMVGHQQPTPVYTQPVCFAPNMMYPVP
                 VSPGVQPLYPIPMTPMPVNQAKTYRAVPNMPQQRQDQHHQSAMMHPASAAGPPIAATP
                 PAYSTQYVAYSPQQFPNQPLVQHVPHYQSQHPHVYSPVIQGNARMMAPPTHAQPGLVS
                 SSATQYGAHEQTHAMYACPKLPYNKETSPSFYFAISTGSLAQQYAHPNATLHPHTPHP
                 QPSATPTGQQQSQHGGSHPAPSPVQHHQHQAAQALHLASPQQQSAIYHAGLAPTPPSM
                 TPASNTQSPQNSPPAAQQTVFTIHPSHVQPAYTNPPHMAHVPQAHVQSGMVPSHPTAH
                 APMMLMTTQPPGGPQAALAQSALQPIPVSTTAHFPYMTHPSVQAHHQQQL" (SEQ ID NO. 19)
BASE COUNT     1144 a   1380 c   1014 g    943 t
```

FIG 6A

ORIGIN
```
   1 accccccgaga aagcaaccca gcgcgccgcc cgctcctcac gtgtccctcc cggccccggg
  61 gccacctcac gttctgcttc cgtctgaccc ctccgacttc cggtaaagag tccctatccg
 121 cacctccgct cccacccggc gcctcggcgc gccgccctc cgatgcgctc agcggccgca
 181 gctcctcgga gtcccgcggt ggccaccgag tctcgccgct tcgccgcagc caggtggccc
 241 gggtggcgct cgctccagcg gccggcgcgg cggagcgggc ggggcggcgg tggcgcggcc
 301 ccgggaccgt atccctccgc cgccccctccc ccgccggcc ccggcccccc tccctcccgg
 361 cagagctcgc ctccctccgc ctcagactgt tttggtagca acggcaacgg cggcggcgcg
 421 tttcggcccg gctcccggcg gctccttggt ctcggcgggc ctccccgccc cttcgtcgtc
 481 gtccttctcc ccctcgccag cccggcgcc cctccggccg cgccaacccg cgcctcccg
 541 ctcggcgccc gtgcgtcccc gccgcgttcc ggcgtctcct tggcgcgccc ggctcccggc
 601 tgtccccgcc cggcgtgcga gcggtgtat gggcccctca ccatgtcgct gaagcccag
 661 cagcagcagc agcagcagca gcaacagcag cagcagcaac agcagcagca gcagcagcag
 721 cagccgccgc ccgcggctgc caatgtccgc aagcccggcg gcagcggcct tctagcgtcg
 781 cccgccgccg cgccttcgcc gtcctcgtcc tcggtctcct cgtcctcggc cacggctccc
 841 tcctcggtgg tcgcggcgac ctccggcggc gggaggcccg gctgggcag aggtcgaaac
 901 agtaacaaag gactgcctca gtctacgatt tcttttgatg gaatctatgc aaatatgagg
 961 atggttcata tacttacatc agttgttggc tccaaatgtg aagtacaagt gaaaaatgga
1021 ggtatatatg aaggagtttt taaaacttac agtccgaagt gtgattgt acttgatgcc
1081 gcacatgaga aagtacaga atccagttcg gggccgaaac gtgaagaaat aatggagagt
1141 attttgttca aatgttcaga ctttgttgtg gtacagttta aagatatgga ctccagttat
1201 gcaaaagag atgcttttac tgactctgct atcagtgcta aagtgaatgg cgaacacaaa
1261 gagaaggacc tggagccctg ggatgcaggt gaactcacag ccaatgagga acttgaggct
1321 ttggaaaatg acgtatctaa tggatgggat cccaatgata tgtttcgata taatgaagaa
1381 aattatggtg tagtgtctac gtatgatagc agtttatctt cgtatacagt gcccttagaa
1441 agagataact cagaagaatt tttaaaacgg gaagcaaggg caaaccagtt agcagaagaa
1501 attgagtcaa gtgcccagta caaagctcga gtggccctgg aaaatgatga taggagtgag
1561 gaagaaaaat acacagcagt tcagagaaat tccagtgaac gtgaggggca cagcataaac
1621 actaggggaaa ataaatatat tcctcctgga caaagaaata gagaagtcat atcctgggga
1681 agtgggagac agaattcacc gcgtatgggc cagcctgcat cgggctccat gccatcaaga
1741 tccacttctc acacttcaga tttcaacccg aattctggtt cagaccaaag agtagttaat
1801 ggaggtgttc cctggccatc gccttgccca tctccttcct ctcgcccacc ttctcgctac
1861 cagtcaggtc ccaactctct tccacctcgg gcagccaccc ctacacggcc gccctccagg
1921 cccccctcgc ggccatccag accccgtct caccccctcg ctcatggttc tccagctcct
1981 gtctctacta tgcctaaacg catgtcttca gaaggcctc caaggatgtc cccaaaggcc
2041 cagcgacatc ctcgaaatca cagagtttct gctgggaggg gttccatatc cagtggccta
2101 gaatttgtat cccacaaccc acccagtgaa gcagctactc ctccagtagc aaggaccagt
2161 ccctcgggg gaacgtggtc atcagtggtc agtgggttc caagttatc ccctaaaact
2221 catagaccca ggtctcccag acagaacagt attggaaata ccccagtgg gccagttctt
2281 gcttctcccc aagctggtat tattccaact gaagctgttg ccatgcctat tccagctgca
2341 tctcctacgc ctgctagtcc tgcatcgaac agagctgtta ccccttctag tgaggctaaa
2401 gattccaggc ttcaagatca gaggcagaac tctcctgcag ggaataaaga aatattaaa
2461 cccaatgaaa catcacctag cttctcaaaa gctgaaaaca aggtatatc accagttgtt
2521 tctgaacata gaaacagat tgatgattta aagaaattta agaatgattt taggttacag
2581 ccaagttcta cttctgaatc tatggatcaa ctactaaaca aaaatagaga gggagaaaaa
2641 tcaagagatt tgatcaaaga caaattgaa ccaagtgcta aggattcttt cattgaaaat
2701 agcagcagca actgtaccag tggcagcagc aagccgaata gccccagcat ttcccttca
2761 atacttagta acacggagca caagaggga cctgaggtca cttccaagg ggttcagact
2821 tccagcccag catgtaaaca agagaaagac gataaggaag agaagaaaga cgcagctgag
2881 caagttagga aatcaacatt gaatcccaat gcaaaggagt tcaacccacg ttccttctct
2941 cagccaaagc cttctactac cccaacttca cctcggcctc aagcacaacc tagcccatct
3001 atggtgggtc atcaacagcc aactccagtt tatactcagc ctgtttgttt tgcaccaaat
3061 atgatgtatc cagtcccagt gagcccaggc gtgcaacctt tatacccaat acctatgacg
3121 cccatgccag tgaatcaagc caagacatat agagcagtac caaatatgcc ccaacagcgg
3181 caagaccagc atcatcgag tgccatgatg cacccagcgt cagcagcggg cccaccgatt
3241 gcagccaccc caccagctta ctccacgcaa tatgttgcct acagtcctca gcagttccca
3301 aatcagcccc ttgttcagca tgtgccacat tatcagtctc agcatcctca tgtctatagt
3361 cctgtaatac agggtaatgc tagaatgatg gcaccaccaa cacacgccca gcctggttta
3421 gtatcttctt cagcaactca gtacggggct catgagcaga cgcatgcgat gtatgcatgt
3481 cccaaattac catacaacaa ggagacaagc ccttctttct actttgccat ttccacgggc
3541 tcccttgctc agcagtatgc gcacctaac gctaccctgc acccacatac tccacacct
3601 cagccttcag ctaccccac tggacagcag caaagccaac atggtggaag tcatcctgca
3661 cccagtcctg ttcagcacca tcagcaacca gccgccagg ctctccatct ggccagtcca
3721 cagcagcagt cagccattta ccacgcgggg cttgcgccaa ctccacccctc catgacacct
3781 gcctccaaca cgcagtcgcc acagaatagt tcccagcag cacaacagac tgtctttacg
3841 atccatcctt ctcacgttca gccggcgtat accaacccac cccacatggc ccacgtacct
3901 caggctcatg tacagtcagg aatggttcct tctcatccaa ctgccatgc gccaatgatg
3961 ctaatgacga cacagccacc cggcggtccc caggccgccc tcgctcaaag tgcactacag
4021 cccattccag tctcgacaac agcgcattc cctatatga cgcacccttc agtacaagcc
4081 caccaccaac agcagttgta aggctgccct ggaggaaccg aaaggccaaa ttccctcctc
4141 ccttctactg cttctaccaa ctggaagcac agaaaactag aatttcattt attttgtttt
4201 taaaatatat atgttgattt cttgtaacat ccaataggaa tgctaacagt tcacttgcag
4261 tggaagatac ttggaccgag tagaggcatt taggaacttg ggggctattc cataattcca
4321 tatgctgttt cagagtcccg caggtaccc agctctgctt gccgaaactg gaagttattt
4381 attttttaat aaccccttgaa agtcatgaac acatcagcta gcaaaagaag taacaagagt
4441 gattcttgct gctattactg ctaaaaaaaa aaaaaaaaaa a     (SEQ ID NO: 20)
```

*FIG 6B*

SEQUENCE LISTING

```
<160> NUMBER OF SEQ ID NOS: 20

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Primer for
      amplification of SCA2 gene region containing one or more
      polymorphic sites
<220> FEATURE:

<400> SEQUENCE: 1
ctccgcctca gactgttttg gtag                                          24

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Primer for
      amplification of SCA2 gene region containing one
      or more polymorphic sites

<400> SEQUENCE: 2
gtggccgagg acgaggagac                                               20

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Primer for
      detection of allelic variants of  SCA2 gene

<400> SEQUENCE: 3
ctcggcgggc ctccccgccc cttcgtcgtc c                                  31

<210> SEQ ID NO 4
<211> LENGTH: 31
<212> TYPE: DNA
<213> ORGANISM: Artificial Sequence
<220> FEATURE:
```

```
<223> OTHER INFORMATION: Description of Artificial Sequence: Allele
      specific primer for detection of allelic variants of SCA2 gene

<400> SEQUENCE: 4
ctcggcgggc ctccccgccc cttcgtcgtc g                                    31

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Allele
      specific primer for detection of allelic variants of SCA2 gene

<400> SEQUENCE: 5
cctccccgcc ccttcgtcgt c                                               21

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Allele
      specific primer for detection of allelic variants of SCA2 gene

<400> SEQUENCE: 6
cgccaacccg cgcctccccg ctcggcgccc gc                                   32

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Allele
      specific primer for detection of allelic variants of SCA2 gene

<400> SEQUENCE: 7
cgccaacccg cgcctccccg ctcggcgccc gt                                   32

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Allele
      specific probe  for detection of allelic variants of SCA2 gene

<400> SEQUENCE: 8
gcgcctcccc gctcggcgcc cg                                              22

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence:Allele
      specific probe  for detection of allelic variants of SCA2 gen

<400> SEQUENCE: 9
ccccttcgtc gtcctccttc tccccct                                         27

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:Allele
``` specific probe for detection of allelic variants of SCA2 genE

<400> SEQUENCE: 10
ccccttcgtc gtcgtccttc tccccct    27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:Allele
      specific probe for detection of allelic variants of SCA2 gene

<400> SEQUENCE: 11
cgctcggcgc ccgcgcgtcc ccgccgc    27

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence:Allele
      specific probe for detection of allelic variants of SCA2 gene

<400> SEQUENCE: 12
cgctcggcgc ccgtgcgtcc ccgccgc    27

<210> SEQ ID NO 13
<211> LENGTH: 459
<212> TYPE: DNA
<213> ORGANISM: Artificial Sequence
<220> FEATURE:
<223> OTHER INFORMATION: Description of Artificial Sequence:Description
      of Artificial derived nucleotide sequence of allelic variant of
      SCA2 gene

<400> SEQUENCE: 13
ctccgcctca gactgttttg gtagcaacgg caacggcggc ggcgcgtttc ggcccggctc    60
ccggcggctc cttggtctcg gcgggcctcc ccgcccttc gtcgtcctcc ttctccccct    120
cgccagcccg ggcgcccctc cggccgcgcc aacccgcgcc tccccgctcg gcgcccgcgc    180
gtccccgccg cgttccggcg tctccttggc gcgcccggct cccggctgtc ccgcccggc    240 gtgcgagccg gtgtatgggc ccctcaccat gtcgctgaag ccccagcagc agcagcagca    300
gcagcagcaa cagcagcagc agcaacagca gcagcagcag cagcagcagc cgccgcccgc    360
ggctgccaat gtccgcaagc ccggcggcag cggccttcta gcgtcgcccg ccgccgcgcc    420
ttcgccgtcc tcgtcctcgg tctcctcgtc ctcggccac    459

<210> SEQ ID NO 14
<211> LENGTH: 106
<212> TYPE: DNA
<213> ORGANISM: Artificial Sequence
<220> FEATURE:
<223> OTHER INFORMATION: Description of Artificial Sequence: Flanking
      sequence Human ataxin-2 gene

<400> SEQUENCE: 14
ctccgcctca gactgttttg gtagcaacgg caacggcggc ggcgcgtttc ggcccggctc    60
ccggcggctc cttggtctcg gcgggcctcc ccgcccttc gtcgtc    106

<210> SEQ ID NO 15
<211> LENGTH: 169
<212> TYPE: DNA

<213> ORGANISM: Artificial Sequence
<220> FEATURE:
<223> OTHER INFORMATION: Description of Artificial Sequence: Flanking
      sequence Human ataxin-2 gene

<400> SEQUENCE:

tccttctccc cctcgccagc ccgggcgccc ctccggccgc gccaacccgc gcctccccgc    60
tcggcgcccg tgcgtccccg ccgcgttccg gcgtctcctt ggcgcgcccg gctcccggct    120
gtccccgccc ggcgtgcgag ccggtgtatg ggcccctcac catgtcgct              169

<210> SEQ ID NO 16
<211> LENGTH: 183
<212> TYPE: DNA
<213> ORGANISM: Artificial Sequence
<220> FEATURE:
<223> OTHER INFORMATION: Description of Artificial Sequence: Flanking
      sequence Human ataxin-2 gene

<400> SEQUENCE: 16
gaagccccag cagcagcagc agcagcagca gcaacagcag cagcagcaac agcagcagca    60
gcagcagcag cagccgccgc ccgcggctgc caatgtccgc aagcccggcg gcagcggcct    120
tctagcgtcg cccgccgccg cgccttcgcc gtcctcgtcc tcggtctcct cgtcctcggc    180
cac                                                                  183

<210> SEQ ID NO 17
<211> LENGTH: 177
<212> TYPE: DNA
<213> ORGANISM: Artificial Sequence
<220> FEATURE:
<223> OTHER INFORMATION: Description of Artificial Sequence: Flanking
      sequence Human ataxin-2 gene

<400> SEQUENCE: 17
ctccgcctca gactgttttg gtagcaacgg caacggcggc ggcgcgtttc ggcccggctc    60
ccggcggctc cttggtctcg gcgggcctcc ccgccccttc gtcgtcgtcc ttctcccct    120 cgccagcccg ggcgccctc cggccgcgcc aaccgcgcc tccccgctcg gcgcccg        177

<210> SEQ ID NO 18
<211> LENGTH: 98
<212> TYPE: DNA
<213> ORGANISM: Artificial Sequence
<220> FEATURE:
<223> OTHER INFORMATION: Description of Artificial Sequence: Flanking
      sequence Human ataxin-2 gene

<400> SEQUENCE: 18
gcgtccccgc cgcgttccgg cgtctccttg gcgcgcccgg ctcccggctg tccccgcccg    60
gcgtgcgagc cggtgtatgg gcccctcacc atgtcgct                            98

<210> SEQ ID NO 19
<211> LENGTH: 1312
<212> TYPE: PRT
<213> ORGANISM: Homo sapiens

<400> SEQUENCE: 19

Met Arg Ser Ala Ala Ala Ala Pro Arg Ser Pro Ala Val Ala Thr Glu
1               5                   10                  15

Ser Arg Arg Phe Ala Ala Ala Arg Trp Pro Gly Trp Arg Ser Leu Gln
                20                  25                  30

Arg Pro Ala Arg Arg Ser Gly Arg Gly Gly Gly Ala Ala Pro Gly

-continued

```
                    35                  40                  45
Pro Tyr Pro Ser Ala Ala Pro Pro Pro Gly Pro Gly Pro Pro Pro
         50                  55                  60
Ser Arg Gln Ser Ser Pro Pro Ser Ala Ser Asp Cys Phe Gly Ser Asn
 65                  70                  75                  80
Gly Asn Gly Gly Gly Ala Phe Arg Pro Gly Ser Arg Arg Leu Leu Gly
                 85                  90                  95
Leu Gly Gly Pro Pro Arg Pro Phe Val Val Leu Leu Pro Leu Ala
                100                 105                 110
Ser Pro Gly Ala Pro Pro Ala Ala Pro Thr Arg Ala Ser Pro Leu Gly
            115                 120                 125
Ala Arg Ala Ser Pro Pro Arg Ser Gly Val Ser Leu Ala Arg Pro Ala
        130                 135                 140
Pro Gly Cys Pro Arg Pro Ala Cys Glu Pro Val Tyr Gly Pro Leu Thr
145                 150                 155                 160
Met Ser Leu Lys Pro Gln Gln Gln Gln Gln Gln Gln Gln Gln Gln
                165                 170                 175
Gln Gln Gln Gln Gln Gln Gln Gln Gln Pro Pro Ala Ala
            180                 185                 190
Ala Asn Val Arg Lys Pro Gly Gly Ser Gly Leu Leu Ala Ser Pro Ala
        195                 200                 205
Ala Ala Pro Ser Pro Ser Ser Ser Val Ser Ser Ser Ala Thr
    210                 215                 220
Ala Pro Ser Ser Val Val Ala Ala Thr Ser Gly Gly Arg Pro Gly
225                 230                 235                 240
Leu Gly Arg Gly Arg Asn Ser Asn Lys Gly Leu Pro Gln Ser Thr Ile
                245                 250                 255
Ser Phe Asp Gly Ile Tyr Ala Asn Met Arg Met Val His Ile Leu Thr
            260                 265                 270
Ser Val Val Gly Ser Lys Cys Glu Val Gln Val Lys Asn Gly Gly Ile
        275                 280                 285
Tyr Glu Gly Val Phe Lys Thr Tyr Ser Pro Lys Cys Asp Leu Val Leu
    290                 295                 300
Asp Ala Ala His Glu Lys Ser Thr Glu Ser Ser Ser Gly Pro Lys Arg
305                 310                 315                 320
Glu Glu Ile Met Glu Ser Ile Leu Phe Lys Cys Ser Asp Phe Val Val
                325                 330                 335
Val Gln Phe Lys Asp Met Asp Ser Ser Tyr Ala Lys Arg Asp Ala Phe
            340                 345                 350
Thr Asp Ser Ala Ile Ser Ala Lys Val Asn Gly Glu His Lys Glu Lys
        355                 360                 365
Asp Leu Glu Pro Trp Asp Ala Gly Glu Leu Thr Ala Asn Glu Glu Leu
    370                 375                 380
Glu Ala Leu Glu Asn Asp Val Ser Asn Gly Trp Asp Pro Asn Asp Met
385                 390                 395                 400
Phe Arg Tyr Asn Glu Glu Asn Tyr Gly Val Val Ser Thr Tyr Asp Ser
                405                 410                 415
Ser Leu Ser Ser Tyr Thr Val Pro Leu Glu Arg Asp Asn Ser Glu Glu
            420                 425                 430
Phe Leu Lys Arg Glu Ala Arg Ala Asn Gln Leu Ala Glu Glu Ile Glu
        435                 440                 445
Ser Ser Ala Gln Tyr Lys Ala Arg Val Ala Leu Glu Asn Asp Asp Arg
    450                 455                 460
```

-continued

```
Ser Glu Glu Glu Lys Tyr Thr Ala Val Gln Arg Asn Ser Ser Glu Arg
465                 470                 475                 480

Glu Gly His Ser Ile Asn Thr Arg Glu Asn Lys Tyr Ile Pro Pro Gly
            485                 490                 495

Gln Arg Asn Arg Glu Val Ile Ser Trp Gly Ser Gly Arg Gln Asn Ser
            500                 505                 510

Pro Arg Met Gly Gln Pro Gly Ser Gly Ser Met Pro Ser Arg Ser Thr
            515                 520                 525

Ser His Thr Ser Asp Phe Asn Pro Asn Ser Gly Ser Asp Gln Arg Val
            530                 535                 540

Val Asn Gly Gly Val Pro Trp Pro Ser Pro Cys Pro Ser Pro Ser Ser
545                 550                 555                 560

Arg Pro Pro Ser Arg Tyr Gln Ser Gly Pro Asn Ser Leu Pro Pro Arg
                565                 570                 575

Ala Ala Thr Pro Thr Arg Pro Pro Ser Arg Pro Ser Arg Pro Ser
            580                 585                 590

Arg Pro Pro Ser His Pro Ser Ala His Gly Ser Pro Ala Pro Val Ser
            595                 600                 605

Thr Met Pro Lys Arg Met Ser Ser Glu Gly Pro Pro Arg Met Ser Pro
            610                 615                 620

Lys Ala Gln Arg His Pro Arg Asn His Arg Val Ser Ala Gly Arg Gly
625                 630                 635                 640

Ser Ile Ser Ser Gly Leu Glu Phe Val Ser His Asn Pro Pro Ser Glu
                645                 650                 655

Ala Ala Thr Pro Pro Val Ala Arg Thr Ser Pro Ser Gly Gly Thr Trp
            660                 665                 670

Ser Ser Val Val Ser Gly Val Pro Arg Leu Ser Pro Lys Thr His Arg
            675                 680                 685

Pro Arg Ser Pro Arg Gln Asn Ser Ile Gly Asn Thr Pro Ser Gly Pro
690                 695                 700

Val Leu Ala Ser Pro Gln Ala Gly Ile Ile Pro Thr Glu Ala Val Ala
705                 710                 715                 720

Met Pro Ile Pro Ala Ala Ser Pro Thr Pro Ala Ser Pro Ala Ser Asn
            725                 730                 735

Arg Ala Val Thr Pro Ser Ser Glu Ala Lys Asp Ser Arg Leu Gln Asp
            740                 745                 750

Gln Arg Gln Asn Ser Pro Ala Gly Asn Lys Glu Asn Ile Lys Pro Asn
            755                 760                 765

Glu Thr Ser Pro Ser Phe Ser Lys Ala Glu Asn Lys Gly Ile Ser Pro
770                 775                 780

Val Val Ser Glu His Arg Lys Gln Ile Asp Asp Leu Lys Lys Phe Lys
785                 790                 795                 800

Asn Asp Phe Arg Leu Gln Pro Ser Ser Thr Ser Glu Ser Met Asp Gln
            805                 810                 815

Leu Leu Asn Lys Asn Arg Glu Gly Glu Lys Ser Arg Asp Leu Ile Lys
            820                 825                 830

Asp Lys Ile Glu Pro Ser Ala Lys Asp Ser Phe Ile Glu Asn Ser Ser
            835                 840                 845

Ser Asn Cys Thr Ser Gly Ser Ser Lys Pro Asn Ser Pro Ser Ile Ser
            850                 855                 860

Pro Ser Ile Leu Ser Asn Thr Glu His Lys Arg Gly Pro Glu Val Thr
865                 870                 875                 880
```

-continued

```
Ser Gln Gly Val Gln Thr Ser Ser Pro Ala Cys Lys Gln Glu Lys Asp
                885                 890                 895

Asp Lys Glu Glu Lys Lys Asp Ala Ala Glu Gln Val Arg Lys Ser Thr
            900                 905                 910

Leu Asn Pro Asn Ala Lys Glu Phe Asn Pro Arg Ser Phe Ser Gln Pro
            915                 920                 925

Lys Pro Ser Thr Thr Pro Thr Ser Pro Arg Pro Gln Ala Gln Pro Ser
930                 935                 940

Pro Ser Met Val Gly His Gln Gln Pro Thr Pro Val Tyr Thr Gln Pro
945                 950                 955                 960

Val Cys Phe Ala Pro Asn Met Met Tyr Pro Val Pro Val Ser Pro Gly
                965                 970                 975

Val Gln Pro Leu Tyr Pro Ile Pro Met Thr Pro Met Pro Val Asn Gln
            980                 985                 990

Ala Lys Thr Tyr Arg Ala Val Pro  Asn Met Pro Gln Gln  Arg Gln Asp
            995                 1000                1005

Gln His  His Gln Ser Ala Met  Met His Pro Ala Ser  Ala Ala Gly
    1010                1015                1020

Pro Pro  Ile Ala Ala Thr Pro  Pro Ala Tyr Ser Thr  Gln Tyr Val
    1025                1030                1035

Ala Tyr  Ser Pro Gln Gln Phe  Pro Asn Gln Pro Leu  Val Gln His
    1040                1045                1050

Val Pro  His Tyr Gln Ser Gln  His Pro His Val Tyr  Ser Pro Val
    1055                1060                1065

Ile Gln  Gly Asn Ala Arg Met  Met Ala Pro Pro Thr  His Ala Gln
    1070                1075                1080

Pro Gly  Leu Val Ser Ser Ser  Ala Thr Gln Tyr Gly  Ala His Glu
    1085                1090                1095

Gln Thr  His Ala Met Tyr Ala  Cys Pro Lys Leu Pro  Tyr Asn Lys
    1100                1105                1110

Glu Thr  Ser Pro Ser Phe Tyr  Phe Ala Ile Ser Thr  Gly Ser Leu
    1115                1120                1125

Ala Gln  Gln Tyr Ala His Pro  Asn Ala Thr Leu His  Pro His Thr
    1130                1135                1140

Pro His  Pro Gln Pro Ser Ala  Thr Pro Thr Gly Gln  Gln Gln Ser
    1145                1150                1155

Gln His  Gly Gly Ser His Pro  Ala Pro Ser Pro Val  Gln His His
    1160                1165                1170

Gln His  Gln Ala Ala Gln Ala  Leu His Leu Ala Ser  Pro Gln Gln
    1175                1180                1185

Gln Ser  Ala Ile Tyr His Ala  Gly Leu Ala Pro Thr  Pro Pro Ser
    1190                1195                1200

Met Thr  Pro Ala Ser Asn Thr  Gln Ser Pro Gln Asn  Ser Phe Pro
    1205                1210                1215

Ala Ala  Gln Gln Thr Val Phe  Thr Ile His Pro Ser  His Val Gln
    1220                1225                1230

Pro Ala  Tyr Thr Asn Pro Pro  His Met Ala His Val  Pro Gln Ala
    1235                1240                1245

His Val  Gln Ser Gly Met Val  Pro Ser His Pro Thr  Ala His Ala
    1250                1255                1260

Pro Met  Met Leu Met Thr Thr  Gln Pro Pro Gly Gly  Pro Gln Ala
    1265                1270                1275

Ala Leu  Ala Gln Ser Ala Leu  Gln Pro Ile Pro Val  Ser Thr Thr
```

| | | |
|---|---|---|
| 1280 | 1285 | 1290 |

Ala His Phe Pro Tyr Met Thr His Pro Ser Val Gln Ala His His
 1295        1300       1305

Gln Gln Gln Leu
 1310

<210> SEQ ID NO 20
<211> LENGTH: 4481
<212> TYPE: DNA
<213> ORGANISM: Homo sapiens

<400> SEQUENCE: 20

| | | | | | |
|---|---|---|---|---|---|
| acccccgaga | aagcaaccca | gcgcgccgcc | cgctcctcac | gtgtccctcc | cggccccggg | 60 |
| gccacctcac | gttctgcttc | cgtctgaccc | ctccgacttc | cggtaaagag | tccctatccg | 120 |
| cacctccgct | cccacccggc | gcctcggcgc | gcccgccctc | cgatgcgctc | agcggccgca | 180 |
| gctcctcgga | gtcccgcggt | ggccaccgag | tctcgccgct | tcgccgcagc | caggtggccc | 240 |
| gggtggcgct | cgctccagcg | gccggcgcgg | cggagcgggc | ggggcggcgg | tggcgcggcc | 300 |
| ccgggaccgt | atccctccgc | cgcccctccc | cgcccggcc | ccggccccccc | tccctcccgg | 360 |
| cagagctcgc | ctccctccgc | ctcagactgt | tttggtagca | acggcaacgg | cggcggcgcg | 420 |
| tttcggcccg | gctccggcg | gctccttggt | ctcggcgggc | ctccccgccc | cttcgtcgtc | 480 |
| gtccttctcc | ccctcgccag | cccgggcgcc | cctccggccg | cgccaacccg | cgcctccccg | 540 |
| ctcggcgccc | gtgcgtcccc | gccgcgttcc | ggcgtctcct | tggcgcgccc | ggctcccggc | 600 |
| tgtccccgcc | cggcgtgcga | gccggtgtat | gggcccctca | ccatgtcgct | gaagccccag | 660 |
| cagcagcagc | agcagcagca | gcaacagcag | cagcagcaac | agcagcagca | gcagcagcag | 720 |
| cagccgccgc | ccgcggctgc | caatgtccgc | aagcccggcg | gcagcggcct | tctagcgtcg | 780 |
| cccgccgccg | cgccttcgcc | gtcctcgtcc | tcggtctcct | cgtcctcggc | cacggctccc | 840 |
| tcctcggtgg | tcgcggcgac | ctccggcggc | gggaggcccg | gcctgggcag | aggtcgaaac | 900 |
| agtaacaaag | gactgcctca | gtctacgatt | tcttttgatg | gaatctatgc | aaatatgagg | 960 |
| atggttcata | tacttacatc | agttgttggc | tccaaatgtg | aagtacaagt | gaaaaatgga | 1020 |
| ggtatatatg | aaggagtttt | taaaacttac | agtccgaagt | gtgatttggt | acttgatgcc | 1080 |
| gcacatgaga | aaagtacaga | atccagttcg | gggccgaaac | gtgaagaaat | aatggagagt | 1140 |
| attttgttca | aatgttcaga | ctttgttgtg | gtacagttta | aagatatgga | ctccagttat | 1200 |
| gcaaaaagag | atgcttttac | tgactctgct | atcagtgcta | aagtgaatgg | cgaacacaaa | 1260 |
| gagaaggacc | tggagccctg | ggatgcaggt | gaactcacag | ccaatgagga | acttgaggct | 1320 |
| ttggaaaatg | acgtatctaa | tggatgggat | cccaatgata | tgtttcgata | taatgaagaa | 1380 |
| aattatggtg | tagtgtctac | gtatgatagc | agtttatctt | cgtatacagt | gcccttagaa | 1440 |
| agagataact | cagaagaatt | tttaaaacgg | gaagcaaggg | caaaccagtt | agcagaagaa | 1500 |
| attgagtcaa | gtgcccagta | caaagctcga | gtggccctgg | aaaatgatga | taggagtgag | 1560 |
| gaagaaaaat | acacagcagt | tcagagaaat | tccagtgaac | gtgagggggca | cagcataaac | 1620 |
| actagggaaa | ataaatatat | tcctcctgga | caaagaaata | gagaagtcat | atcctgggga | 1680 |
| agtgggagac | agaattcacc | gcgtatgggc | cagcctggat | cgggctccat | gccatcaaga | 1740 |
| tccacttctc | acacttcaga | tttcaacccg | aattctggtt | cagaccaaag | agtagttaat | 1800 |
| ggaggtgttc | cctggccatc | gccttgccca | tctccttcct | ctcgcccacc | ttctcgctac | 1860 |
| cagtcaggtc | ccaactctct | tccacctcgg | gcagccaccc | ctacacggcc | gccctccagg | 1920 |

```
cccccctcgc ggccatccag accccgtct caccccctctg ctcatggttc tccagctcct    1980
gtctctacta tgcctaaacg catgtcttca gaagggcctc caaggatgtc cccaaaggcc    2040
cagcgacatc ctcgaaatca cagagtttct gctgggaggg gttccatatc cagtggccta    2100
gaatttgtat cccacaaccc acccagtgaa gcagctactc ctccagtagc aaggaccagt    2160
ccctcggggg gaacgtggtc atcagtggtc agtggggttc caagattatc ccctaaaact    2220
catagaccca ggtctcccag acagaacagt attggaaata cccccagtgg gccagttctt    2280
gcttctcccc aagctggtat tattccaact gaagctgttg ccatgcctat tccagctgca    2340
tctcctacgc ctgctagtcc tgcatcgaac agagctgtta cccttctag tgaggctaaa     2400
gattccaggc ttcaagatca gaggcagaac tctcctgcag ggaataaaga aaatattaaa    2460
cccaatgaaa catcacctag cttctcaaaa gctgaaaaca aaggtatatc accagttgtt    2520
tctgaacata gaaaacagat tgatgattta agaaattta agaatgattt taggttacag     2580
ccaagttcta cttctgaatc tatggatcaa ctactaaaca aaaatagaga gggagaaaaa    2640
tcaagagatt tgatcaaaga caaaattgaa ccaagtgcta aggattcttt cattgaaaat    2700
agcagcagca actgtaccag tggcagcagc aagccgaata gccccagcat ttcccttca     2760
atacttagta acacggagca caagagggga cctgaggtca cttcccaagg ggttcagact    2820
tccagcccag catgtaaaca agagaaagac gataaggaag agaagaaaga cgcagctgag    2880
caagttagga aatcaacatt gaatcccaat gcaaaggagt caacccacg ttccttctct     2940
cagccaaagc cttctactac cccaacttca cctcggcctc aagcacaacc tagcccatct    3000
atggtgggtc atcaacagcc aactccagtt tatactcagc ctgtttgttt tgcaccaaat    3060
atgatgtatc cagtcccagt gagcccaggc gtgcaacctt tacccaat acctatgacg      3120
cccatgccag tgaatcaagc caagacatat agagcagtac caaatatgcc caacagcgg    3180
caagaccagc atcatcagag tgccatgatg cacccagcgt cagcagcggg cccaccgatt    3240
gcagccaccc caccagctta ctccacgcaa tatgttgcct acagtcctca gcagttccca    3300
aatcagcccc ttgttcagca tgtgccacat tatcagtctc agcatcctca tgtctatagt    3360
cctgtaatac agggtaatgc tagaatgatg gcaccaccaa cacacgccca gcctggttta    3420
gtatcttctt cagcaactca gtacggggct catgagcaga cgcatgcgat gtatgcatgt   3480
cccaaattac catacaacaa ggagacaagc ccttctttct actttgccat ttccacgggc    3540
tcccttgctc agcagtatgc gcaccctaac gctaccctgc acccacatac tccacaccct    3600
cagccttcag ctaccccac tggacagcag caaagccaac atggtggaag tcatcctgca    3660
cccagtcctg ttcagcacca tcagcaccag gccgcccagg ctctccatct ggccagtcca    3720
cagcagcagt cagccattta ccacgcgggg cttgcgccaa ctccaccctc catgacacct    3780
gcctccaaca cgcagtcgcc acagaatagt ttcccagcag cacaacagac tgtctttacg    3840
atccatcctt ctcacgttca gccggcgtat accaacccac ccacatggc ccacgtacct     3900
caggctcatg tacagtcagg aatggttcct tctcatccaa ctgcccatgc gccaatgatg    3960
ctaatgacga cacagccacc cggcggtccc caggccgccc tcgctcaaag tgcactacag    4020
cccattccag tctcgacaac agcgcatttc ccctatgta cgcacccttc agtacaagcc     4080
caccaccaac agcagttgta aggctgccct ggaggaaccg aaaggccaaa ttcctcctc     4140
ccttctactg cttctaccaa ctggaagcac agaaaactag aatttcattt attttgtttt    4200
taaaatatat atgttgattt cttgtaacat ccaataggaa tgctaacagt tcacttgcag    4260
```

```
tggaagatac ttggaccgag tagaggcatt taggaacttg ggggctattc cataattcca    4320
tatgctgttt cagagtcccg caggtacccc agctctgctt gccgaaactg gaagttattt    4380 atttttaat aacccttgaa agtcatgaac acatcagcta gcaaaagaag taacaagagt     4440
gattcttgct gctattactg ctaaaaaaaa aaaaaaaaaa a                        4481
```

METHOD OF DETECTION OF ALLELIC VARIANTS OF SCA2 GENE

FIELD OF THE INVENTION

The present invention relates to a method of detection for human Spinocerebellar ataxia 2 gene variants, and more particularly their use in applications such as molecular diagnosis, prediction of an individual's disease susceptibility, and the genetic analysis of SCA2 gene in a population. The invention also provides primer and probe sequences useful in detecting these polymorphic variations in SCA2 gene and their use in diagnosis and prediction of an individual's susceptibility to SCA2 disease.

BACKGROUND AND PRIOR ART

Spinocerebellar ataxias (SCAs) are a clinically heterogeneous group of autosomal dominant neurodegenerative disorders characterized by progressive deterioration in balance and coordination. The clinical symptoms include ataxia, dysarthria, ophthalmoparesis, and variable degrees of motor weakness. The symptoms occur due to progressive neuronal loss primarily in the cerebellum but also in other parts of central nervous system. The symptoms usually begin during the third or fourth decade of life, however, juvenile onset has been identified. Typically, the disease worsens gradually, often resulting in complete disability and death 10–20 years after the onset of symptoms. Individuals with juvenile onset spinocerebellar ataxias, however, typically have more rapid progression of the phenotype than the late onset cases.

Seven disease loci have been identified to date as causing this phenotype—Spinocerebellar ataxia 1 (SCA1) (Orr et al., Nat. Genet. 4, 221–226 (1993)), SCA2 (Pulst et al., Nat. Genet. 14, 269–276 (1996); Sanpei et al., Nat. Genet. 14, 227–284 (1996); Imbert et al., Nat. Genet. 14, 285–291 (1996)), SCA3/MJD (Kawaguchi et al., Nat. Genet. 8, 221–227 (1994)), SCA6 (Zhuchenko et al, Nat. Genet. 15,62–68 (1997)), SCA7 (David et al., Nat. Genet. 17, 65–70 (1997)), SCA8 (Koob et al., Nat. Genet. 21, 379–384 (1999)) and SCA12 (Holmes et al., Nat. Genet. 23, 391–392 (1999)). The causative mutation associated with all these disease types is abnormal expansion of trinucleotide repeat motif in their corresponding gene. The expansion of the repeat tract beyond the normal range produces premutation allele that may further expand to disease producing mutations.

The genomes of all organisms undergo spontaneous mutation in the course of their continuing evolution generating variant forms of progenitor sequences (Gusella, Ann. Rev. Biochem. 55, 831–854 (1986)). The variant form may confer an evolutionary advantage or disadvantage relative to a progenitor form or may be neutral. In some instances, a variant form confers a lethal disadvantage and is not transmitted to subsequent generations of the organism. In other instances, a variant form confers an evolutionary advantage to the species, is eventually incorporated into the DNA of many or most members of the species, and effectively becomes the progenitor form. In many instances, both progenitor and variant form(s) survive and co-exist in a species population. The coexistence of multiple forms of a sequence gives rise to polymorphisms. Several different types of polymorphisms have been reported. A restriction fragment length polymorphism (RFLP) means a variation in DNA sequence that alters the length of a restriction fragment as described in Botstein et al., Am. J. Hum. Genet. 32, 314–331 (1980). The restriction fragment length polymorphism may create or delete a restriction site, thus changing the length of the restriction fragment. RFLPs have been widely used in human and animal genetic analyses (Donis-Keller, Cell 51, 319–337 (1987)). Other polymorphisms take the form of short tandem repeats (STRs) that include tandem di-, tri- and tetranucleotide repeated motifs. These tandem repeats are also referred to as variable number tandem repeat (VNTR) polymorphisms. VNTRs have been used in identity and paternity analysis and in a large number of genetic mapping studies.

Other polymorphisms take the form of single nucleotide variations between individuals of the same species. Such polymorphisms are far more frequent than RFLPS, STRs and VNTRs. Some single nucleotide polymorphisms (SNPs) occur in protein-coding sequences, in which case, one of the polymorphic forms may give rise to the expression of a defective or other variant protein and, potentially, a genetic disease. Examples of genes, in which polymorphisms within coding sequences give rise to genetic disease include beta.-globin (sickle cell anemia) and CFTR (cystic fibrosis). Other single nucleotide polymorphisms occur in non-coding regions. Some of these polymorphisms may also result in defective protein expression (e.g., as a result of defective splicing). Other single nucleotide polymorphisms have no phenotypic effects.

SNPs can be used in the same manner as RFLPs, and VNTRs but offer several advantages. SNPs occur with greater frequency and are spaced more uniformly throughout the genome than other forms of polymorphism. The greater frequency and uniformity of SNPs means that there is a greater probability that such a polymorphism will be found in close proximity to a genetic locus of interest than would be the case for other polymorphisms. Also, the different forms of characterized SNPs are often easier to distinguish that other types of polymorphism (e.g., by use of assays employing allele-specific hybridization probes or primers).

Spinocerebellar ataxia 2 (SCA2), which was initially described in a Cuban population (Gispert et al., Nat. Genet. 4, 295–299 (1993)), has now been reported worldwide. The human SCA2 gene has 25 exons and encompasses approximately 130 kb on 12q23-24.1 region of chromosome 12 (Sahba et al., Genomics 47, 359–364 (1998)). The molecular basis of the disease is an expansion of a CAG repeat tract in exon 1 of SCA2 gene. The molecular diagnosis of clinically suspected SCA2 patients is carried out by the correct sizing of the CAG repeats at the SCA2 locus. In normal individuals this CAG repeat is not only polymorphic in length, ranging from 14–31 repeats with a mode of 22 repeats, but also cryptic in nature, having one or more interrupting CAA triplets. In contrast, the SCA2 disease alleles contain a pure, contiguous stretch of 34–59 CAG repeats. Sanpei and Tsuji (patent CA2241173, EP00878543 and WO 98/18920) have provided the cDNA fragments of the gene causative of spinocerebellar ataxia type 2 having a determined base sequence. Pulst and Ramos in patent WO 97/42314 have also provided the isolated nucleic acids encoding human SCA2 protein or fragments thereof and a method of diagnosis of SCA2 disease.

Tsuji and Sanpei have also patented a method for specifically diagnosing SCA2 (patents CA22323 11, EP0869186 and WO 98/03679). Therein the method comprises effecting PCR by employing DNA to be tested as template and using nucleic acid primers hybridizable with the parts of the base sequences of the SCA2 gene. The diagnosis depends on the number of the CAG repeat units in the SCA2 gene, the patient with SCA2 has the number of CAG repeat units of 35 or above while the gene of a normal subject has 15 to 24 repeats, which enables the diagnosis of SCA2.

However, these methods are not useful for detecting normal individuals carrying repeats predisposed to instability and expansion (premutation alleles) as the repeat length alone would not be the correct predictor of repeat instability at SCA2 locus due to presence of varying number of CAA interruptions. The presence of interruptions within the triplet repeats has been shown to play an important role in determining stability to a number of trinucleotide repeat disorders (Chung et al., Nat. Genet. 5, 254–258 (1993); Kunst et al., Cell 77, 853–861 (1994); Eichler et al., Nat. Genet. 8, 88–94 (1994)). It has been proposed that the presence of these interruptions confers stability and their absence predisposes alleles to instability and eventual disease status.

The prior art is lacking in any method that associates the allelic variants of SCA2 gene to the disease susceptibility. The prior art is also lacking in any study that correlates the substructure of SCA2 CAG repeat with repeat instability and predisposition to the SCA2 disease. This is the first demonstration that relates to the detection of single nucleotide polymorphisms in human SCA2 gene and their use for applications such as molecular diagnosis, prediction of an individual's SCA2 disease susceptibility or otherwise, and/or the genetic analysis of SCA2 gene in a population. The novelty of present invention is in providing a method for detecting allelic variants of SCA2 gene within the human population and their association with the disease for prediction of an individual's predisposition to SCA2.

OBJECTS OF THE INVENTION

The main object of the present invention is to provide method of detection of allelic variants of human SCA2 gene.

Another object is to provide allele specific primers and probes useful for detection of allelic variants of human SCA2 gene.

Yet another object of the invention is to provide a method for establishing association of SCA2 allelic variants with disease susceptibility.

Still another object of the invention is to provide a method for screening individuals carrying SCA2 alleles predisposed to instability and expansion.

SUMMARY OF THE INVENTION

The present invention relates to allelic variants of human Spinocerebellar ataxia 2 (SCA2) gene and provides allele-specific primers and probes suitable for detecting these allelic variants for applications such as molecular diagnosis, prediction of an individual's disease susceptibility, and/or the genetic analysis of SCA2 gene in a population.

DETAILED DESCRIPTION OF THE INVENTION

The present invention relates to the detection of the allelic variants of the human SCA2 gene and their utility in predicting an individual's susceptibility to the SCA2 disease.

Accordingly, the present invention provides method detection of human Spinocerebellar ataxia 2 gene variants, said method comprising the steps of:
1. designing and synthesizing oligonucleotide primers for PCR amplification of CAG repeat containing region of exon 1 of human SCA2 gene,
2. amplifying genomic DNA of SCA2 patients and normal control individuals using the above said primers,
3. sequencing the amplified PCR product and identifying sequence variations computationally by comparing it with the already existing sequence of human SCA2 gene,
4. screening normal control individuals and SCA2 patients for novel single nucleotide polymorphisms using allele specific oligonucleotide probes,
5. computing the frequencies of CC and GT haplotypes in normals and SCA2 patients,
6. establishing the association of the CC and GT haplotype with the SCA2 disease based on their frequency distribution in normals and SCA2 patients,
7. predicting the risk or susceptibility to the SCA 2 disease based on the haplotype present at the polymorphic sites in the individual tested, GT haplotype being at low risk and CC haplotype at high risk to the disease.

In an embodiment, the primers suitable for amplification of the SCA2 gene region containing one or more polymorphic sites, are selected from the group consisting of SEQ ID NO: 1, SEQ ID NO: 2, SEQ ID NO: 3, SEQ ID NO: 4, SEQ ID NO:5, SEQ ID NO: 6, SEQ ID NO: 7, SEQ ID NO: 8 and compliments thereof.

In another embodiment, the allele specific oligonucleotide probes useful for detection of SCA2 gene variants are selected from the group consisting of SEQ ID NO: 9, SEQ ID NO: 10, SEQ ID NO: 11, SEQ ID NO: 12 and the compliments thereof, wherein the polymorphic site occupies a central position of the probe.

In yet another embodiment, the length of the oligonucleotide primers and probes is in the range of 5 to 100 bases.

In still another embodiment, allelic variants of SCA2 gene have GT and CC haplotypes, Further, the invention provides a diagnostic kit for the detection of SNP haplotypes (CC/GT) comprising suitable primers and probes selected from polynucleotide sequences under SEQ ID NO: 1 to 12.

In another embodiment of the invention a nucleic acid vector may contain the allelic variants of SCA2 gene.

In an embodiment of the invention primers suitable for amplification of SCA2 gene region containing one or more polymorphic sites are provided, said primers selected from the group comprising:
 a) CTC CGC CTC AGA CTG TTT TGG TAG 3' (as listed in SEQ ID NO: 1); and
 b) GTG GCC GAG GAC GAG GAG AC 3' (as listed in SEQ ID NO: 2) and compliments thereof.

In yet another embodiment of the invention allele specific primers suitable for detection of allelic variants of SCA2 gene are provided, selected from the group comprising:
 a) 5' CTC GGC GGG CCT CCC CGC CCC TTC GTC GTC C 3' (as listed in SEQ ID NO: 3);
 b) 5' CTC GGC GGG CCT CCC CGC CCC TTC GTC GTC G 3' (as listed in SEQ ID NO: 4);
 c) 5' CCT CCC CGC CCC TTC GTC GTC 3' (as listed in SEQ ID NO: 5);
 d) 5' CGC CAA CCC GCG CCT CCC CGC TCG GCG CCC GC 3' (as listed in SEQ ID NO: 6);
 e) 5' CGC CAA CCC GCG CCT CCC CGC TCG GCG CCC GT 3' (as listed in SEQ ID NO: 7); and
 f) 5' GCG CCT CCC CGC TCG GCG CCC G 3' (as listed in SEQ ID NO: 8) and compliments thereof.

In still another embodiment of the invention allele specific probes useful for detection of SCA2 gene variants wherein the polymorphic site occupies a central position of the probe are provided, said allele specific probes selected from the group comprising:
 a) 5' CCC CTT CGT CGT CCT CCT TCT CCC CCT 3' (as listed in SEQ ID NO: 9);
 b) 5' CCC CTT CGT CGT CGT CCT TCT CCC CCT 3' (as listed in SEQ ID NO: 10);

c) 5' CGC TCG GCG CCC GCG CGT CCC CGC CGC 3' (as listed in SEQ ID NO: 11); and d) 5' CGC TCG GCG CCC GTG CGT CCC CGC CGC 3' (as listed in SEQ ID NO: 12) are compliments thereof.

The allelic variants of human SCA2 gene may comprise one or more of the following single nucleotide polymorphisms as compared with the human SCA2 complete cDNA sequence in the data base (GenBank accession number U70323).

TABLE 1

|  | Site of change | Base change | Amino-acid alteration |
|---|---|---|---|
| (A) | 481 | G - C | Val - Leu |
| (B) | 552 | T - C | Arg—Arg |

The sites of change is in accordance with the human SCA2 complete cDNA sequence in the database (GenBank accession number U70323).

The invention also provides a method of analysing a nucleic acid from an individual for the presence of base at any one of the polymorphic sites shown in Table 1. This type of analysis can be performed on a plurality of individuals who are tested either for the presence or for the predisposition to the SCA2 disease. The susceptibility to the disease can then be established based depending on the base or set of bases present at the polymorphic sites in the individuals tested.

The invention also provides oligonucleotide sequences (as listed in SEQ ID NO: 1 to 12) suitable for use as allele specific primers and probes for the detection of polymorphic sites listed in Table 1.

Further, a diagnostic kit comprising one or more of the allele specific primers or probes along with the required buffers and accessories suitable for identification of SCA2 allelic variants to establish an individual's susceptibility to SCA2 disease is also included in the invention.

Eucaryotic expressing vectors comprising a DNA sequence coding for a protein or a peptide according to the invention are new materials and are also included in the invention. Host cells, for example, cloned human cell lines, can be transformed using the new expression vectors and are also included in the invention.

BRIEF DESCRIPTION OF THE DRAWINGS

The manner in which the above-mentioned features, advantages and objects of the invention, as well as others which will become clear, are attained and can be understood in detail, by the particular description of the invention are illustrated in the appended drawings. These drawings form a part of the specification. It is to be noted, however, that the appended drawings illustrate preferred embodiments of the invention and thereof not to be considered limiting in their scope.

In the drawing(s) accompanying this specification:

FIG. 4 shows the details of the SNP with reference ID 695871 submitted by the applicants in the SNP database.

FIG. 5 shows the details of the SNP with reference ID 695872 submitted by the applicants in the SNP database.

FIG. 6 shows the complete cDNA sequence of the human SCA2 MRNA submitted by pulst, S-M in the Genbank database.

Other and further aspects, features, and advantages of the present invention will be apparent from the following description of the preferred embodiments of the invention given for the purpose of disclosure. Alternative embodiments of the invention can be envisaged by those skilled in the art. All such alternative embodiments are intended to lie within the scope of this invention.

I. Novel Polymorphisms of the Invention

As a first step to the present invention, the applicants carried out the PCR amplification of CAG repeat containing region of exon 1 of the human SCA2 gene using new oligonucleotide primers. These primers were designed in accordance with the human SCA2 complete cDNA sequence submitted by Pulst, S. -M. in the data base (GenBank accession number U70323). The sequencing of the purified PCR product revealed two novel single nucleotide polymorphisms (SNPs) in exon 1 of human SCA2 gene. It was apparent, therefore, that there is a hitherto unrecognized allele or subtype of the human SCA2 gene.

The present invention provides a sequence for the allelic variants of human spinocerebellar ataxia 2 (SCA2) gene comprising one or more of the following single nucleotide polymorphisms compared with the human SCA2 complete cDNA sequence in the data base (GenBank accession number U70323).

TABLE 1

|  | Site of change | Base change | Amino-acid alteration |
|---|---|---|---|
| (A) | 481 | G - C | Val - Leu |
| (B) | 552 | T - C | Arg—Arg |

The sites of changes are in accordance with the human SCA2 complete cDNA sequence in the database (GenBank accession number U70323).

(The applicants have already submitted these two SNPs in the SNP database on Aug. 2, 2000. The first SNP at position 481 and having either a G or a C base have a reference SNP ID 695871. The reference SNP ID for the second SNP at position 552 and with T or a C base is 695872).

Figure 1:
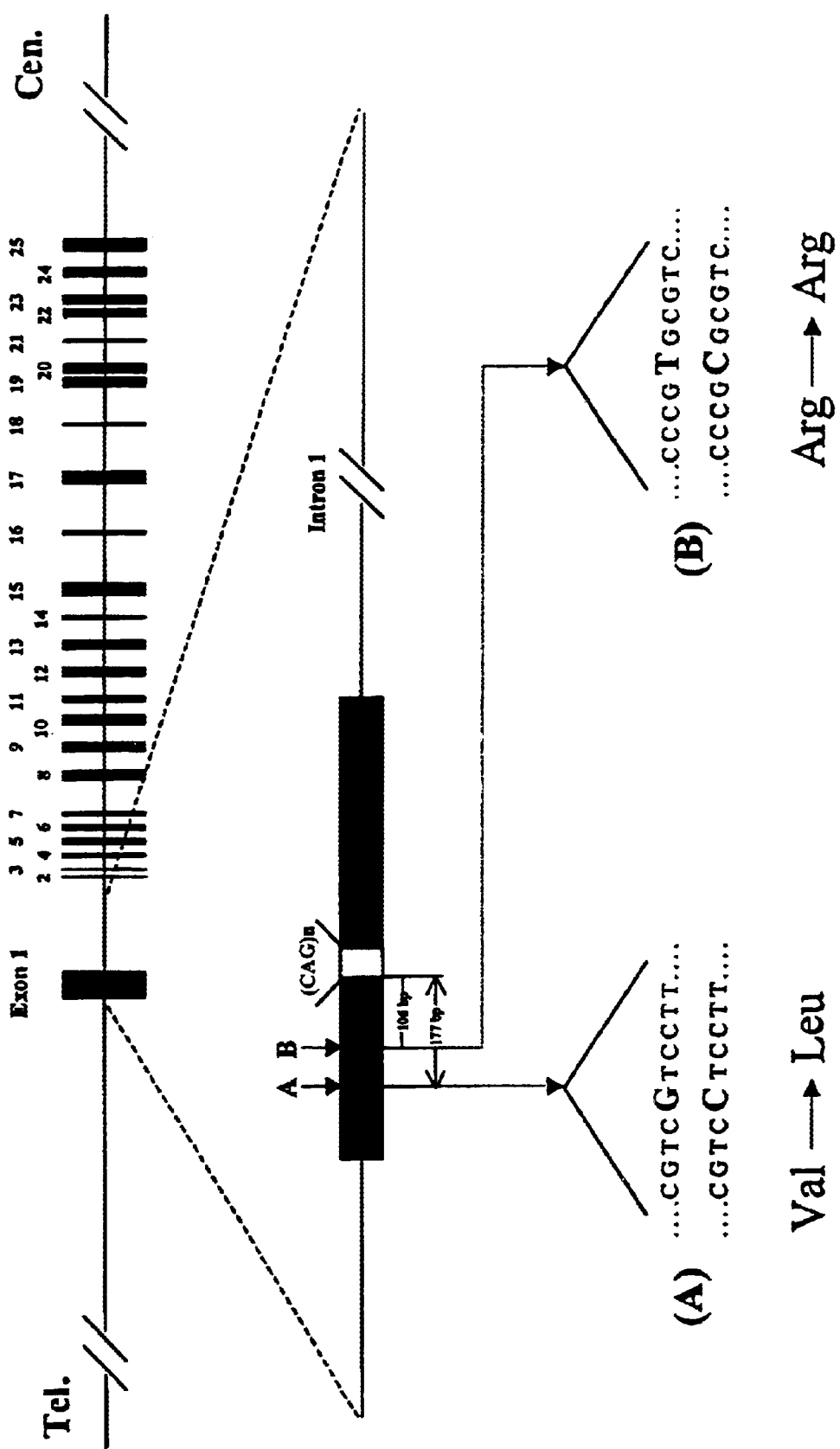
FIG. 1 is a schematic representation of the two novel single nucleotide polymorphisms in SCA2 gene. The top line depicts the position of the 25 exons of the SCA2 gene. The second line shows the relative locations of the two polymorphic sites and the CAG repeat tract in exon 1 of SCA2 gene. Both the polymorphisms are also shown in sequence context below the gene. A depicts bases 10–19 of SEQ ID NO: 10 and bases 10–19 of SEQ ID NO:9. B depicts bases 10–19 of SEQ ID NO:12 and bases 10–19 of SEQ ID NO:11.

The first polymorphic site (A), as shown in FIG. 1, had either a G or a C base and is 177 bp upstream of the polymorphic SCA2 CAG repeat stretch. The second polymorphic site (B) is situated 106 bp upstream of the CAG repeat tract and contains either a T or a C base. While the first substitution changes the amino acid sequence from valine to leucine, the second substitution is neutral.

For example, the nucleotide sequence of the allelic variant of human SCA2 gene having polymorphic sites as listed in Table 1 may be

```
5' C TCC GCC TCA GAC TGT TTT GGT AGC AAC GGC AAC GGC GGC GGC

GCG TTT CGG CCC GGC TCC CGG CGG CTC CTT GGT CTC GGC GGG CCT

CCC CGC CCC TTC GTC GTC CTC CTT CTC CCC CTC GCC AGC CCG GGC GCC

CCT CCG GCC GCG CCA ACC CGC GCC TCC CCG CTC GGC GCC CGC GCG

TCC CCG CCG CGT TCC GGC GTC TCC TTG GCG CGC CCG GCT CCC GGC

TGT CCC CGC CCG GCG TGC GAG CCG GTG TAT GGG CCC CTC ACC ATG

TCG CTG AAG CCC CAG CAG CAG CAG CAG CAG CAG CAG CAA CAG CAG

CAG CAG CAA CAG CAG CAG CAG CAG CAG CAG CAG CCG CCG CCC GCG

GCT GCC AAT GTC CGC AAG CCC GGC GGC AGC GGC CTT CTA GCG TCG

CCC GCC GCC GCG CCT TCG CCG TCC TCG TCC TCG GTC TCC TCG TCC TCG

GCC AC 3' (SEQ ID NO:13)
```

In the above sequence the SNPs (A) and (B) are at nucleotide position 107 and 178 respectively and are shown in bold.

II. Association Analysis with the Disease

Analysis of these two SNPs in 215 normal and 50 expanded SCA2 chromosomes revealed that although four haplotypes are possible with two biallelic polymorphic systems, only two were observed, GT or CC haplotype. No GC or CT allele was detected in our sample set suggesting that either these alleles are very rare or G, T and C, C are exclusively linked to each other. The frequency of each SNP in normal and expanded SCA2 chromosomes is summarized in Table 2.

TABLE 2

| CAG repeat size | No. of chromosomes studied (n) | Percentage GT haplotype (n) | Percentage CC haplotype (n) |
|---|---|---|---|
| Normal (18–31 repeats) | 215 | 70.7% (152) | 29.3% (63) |
| Expanded (>32 repeats) | 50 | 0.0% (0) | 100% (50) |

In 215 normal chromosomes tested, the GT and the CC haplotype was represented in 70.7% and 29.3% respectively. Further studies on expanded chromosomes revealed a highly significant ($\chi^2$=76.589, p<0.0000) difference in the distribution of the two SNPs between the normal and the expanded SCA2 chromosomes (Table 1). All the SCA2 chromosomes (n=50) segregated with CC allele, showing that the disease chromosomes are in complete association with the CC haplotype. In order to establish the molecular basis for the susceptibility of CC alleles for SCA2 expansion mutation, we performed the CAA interspersion analysis of SCA2 CAG repeat stretch for chromosomes with GT and CC haplotype.

Figure 2:
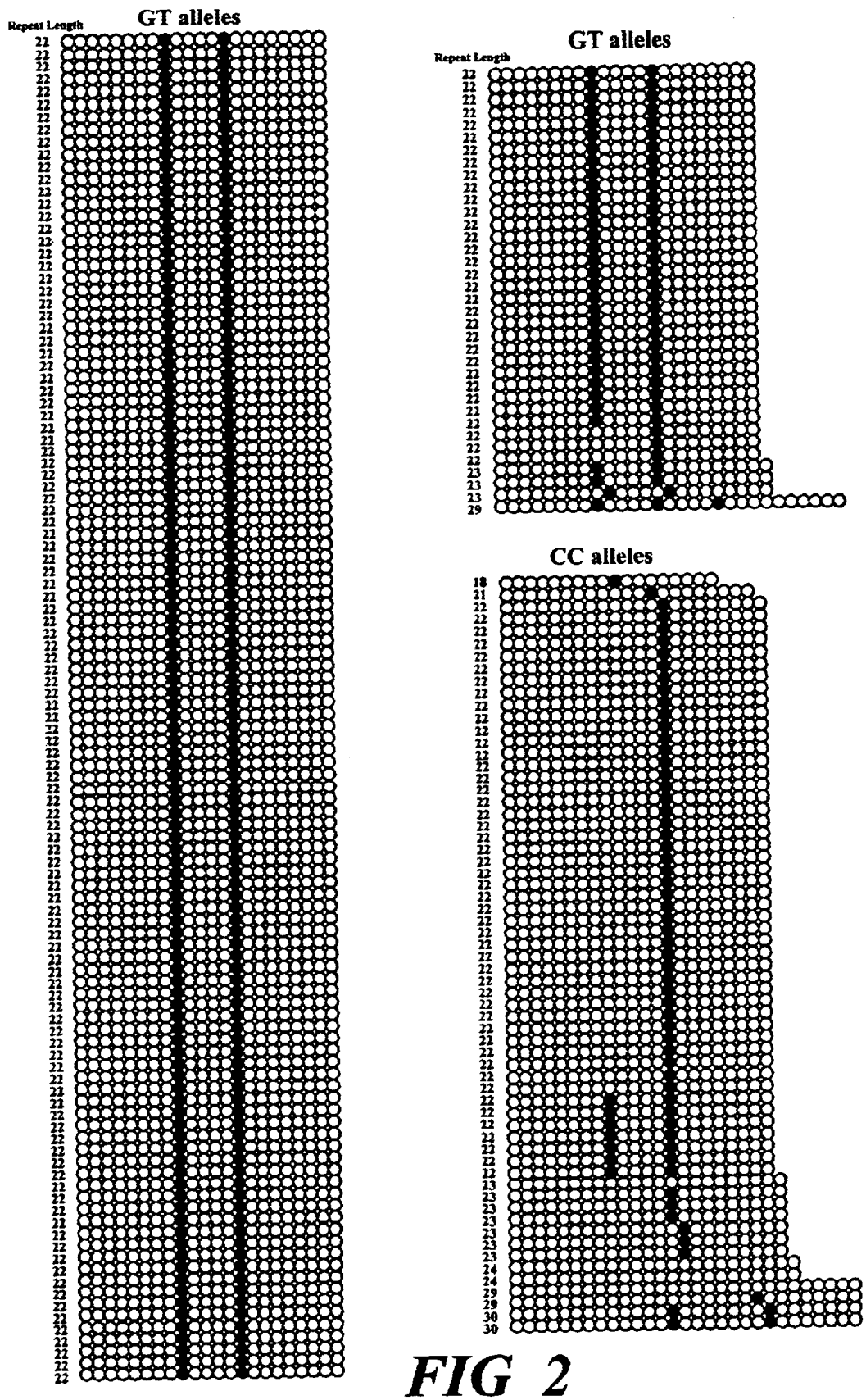
FIG. 2 shows the distribution of CAA triplets in SCA2 CAG repeat tract of 215 normal chromosomes. Open circles represent CAG triplets and dark circles represent CAA triplets. Alleles are grouped by GT or CC haploypes and are arranged in the ascending order of the repeat length.
Figure 3:
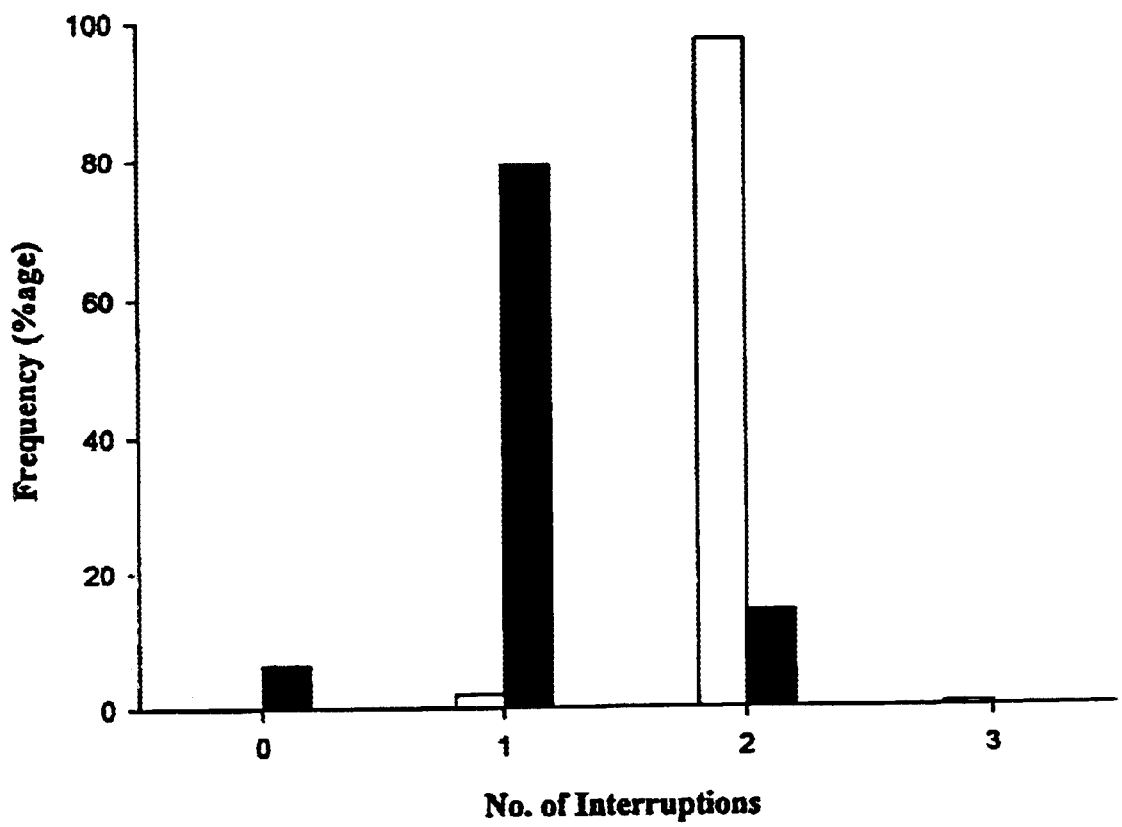
FIG. 3 shows the frequency distribution of CAA interruptions in normal SCA2 chromosomes with GT (open bar) and CC haplotype (filled bars). Frequencies on Y-axis are the percentage of 152 alleles with GT haplotype or 63 alleles with CC haplotype.

Among the total of 215 control chromosomes analysed for CAA interspersion pattern, 1.8% (4/215) contained none, 20.9% (53/215) had one, 76.7% (157/215) had two and 0.5% (1/215) had three CAA interruptions (FIG. 2). A marked split was observed in the number and the pattern of CAA interruptions in the alleles with GT and CC haplotype. 98% (149/152) of the chromosomes with GT alleles had two or more CAA interruptions while 86% (54/63) of the CC alleles had either one or were devoid of interruption. This difference in the number of interruptions present on GT and CC alleles as shown graphically in FIG. 3, is quite significant.

The first 5' CAA interruption was observed at the triplet position 9 and the second at position 14 in 97.4% (148/152) of the GT alleles. In contrast, 73% (46/63) of the CC alleles had their first 5' interruption at position 14 suggesting that absence of the most proximal 5' CAA interruption. Again a significant difference in the position of the first CAA interruption was observed between the two SNP haplotypes.

When similar length normal chromosomes with GT and the CC haplotypes were compared by CAA interspersion pattern, the CC alleles were found to have less number of interruptions than the GT alleles. And this has resulted in a concomitant increase in pure CAG repeat length in chromosomes with CC haplotype. Similarly for 215 randomly selected normal chromosomes (FIG. 2), the average length of the longest uninterrupted CAG repeat tract was significantly larger (one tailed t test, p=0.0000) in CC alleles (13.3 repeats) as compared to GT alleles (8.03 repeats).

It has been proposed that a minimal length of pure repeats is required to initiate instability at a repeat locus. The presence of interruptions breaks the repeats into smaller repeat tracts and thus protects the repeat from instability by reducing the length of continuous uninterrupted repeats. There are evidences in case of SCA1 and fragile X syndrome that larger uninterrupted repeats are more likely to expand than cryptic repeats. This is also true for dinucleotide repeats where the degree of polymorphism for a repeat locus is generally proportional to the length of the perfect repeat. Since 98% of the normal chromosomes with GT haplotype have two or more CAA interruptions while majority of the alleles with a single or no CAA interruptions are found to be associated with CC haplotype (FIG. 3), suggests that absence of CAA interruptions between the CAG repeat tract is one of the factors contributing to repeat instability and facilitating repeat expansion in chromosomes with CC haplotype. This is further supported by the observation that the average length of the longest uninterrupted repeat tract is much longer in CC alleles (13.3 repeats) compared to GT alleles (8.03 repeats). The length of repeat variability also reduced with an increase in over all number of interruptions. For example, the length of the uninterrupted CAG repeat tract in alleles with one interruption and CC haplotype extends from 5–22, whereas for alleles with two or more CAA interruption and the GT haplotype, the range is 8–13 pure CAG repeats.

Therefore, haplotype analysis carried out using two novel SNPs suggested that both the CAG repeat length and its substructure are important parameters in the assessment of stability of SCA2 repeat alleles. The presence of CAA interruptions at SCA2 locus play an important role in determining stability to CAG repeats and their absences predisposes alleles to expansion and eventually to disease status. A complete association of CC haplotype with SCA2 expanded chromosomes and the presence of only one or no interrupting CAA triplet in control chromosomes with CC haplotype indicates that this novel allelic variant of SCA2 allele is predisposed to expansion. In other words, the absence of GT haplotype in expanded chromosomes suggests that the GT alleles are at nearly zero risk for SCA2 disease. Therefore, these SNP haplotypes in the human SCA2 gene could be used as a method of establishing individual risk to SCA2. Moreover, the presence of these two novel SNPs in very close proximity to the SCA2 repeat region also makes them very useful genetic markers in studying the origin and the evolution of SCA2 expansion mutation. The association of the CC/GT haplotypes with the SCA2 disease was studies in an Indian population. However similar association, i.e., GT haplotype being at low risk and CC being at high risk for SCA2 disease, can be expected to hold true for other human populations also.

III. Diagnostic Kits

The invention further provides diagnostic kit comprising at least one or more allele-specific oligonucleotide as described in SEQ ID 1 to 12. Often, the kits contain one or more pairs of allele-specific oligonucleotides hybridizing to different forms of a polymorphism. In some kits, the allele-specific oligonucleotides are provided immobilized to a substrate. For example, the same substrate can comprise allele-specific oligonucleotide probes for detecting at least one or all of the polymorphisms shown in Table 1. Optional additional components of the kit include, for example, restriction enzymes, reverse-transcriptase or polymerase, the substrate nucleoside triphosphates, means used to label (for example, an avidinenzyme conjugate and enzyme substrate and chromogen if the label is biotin), and the appropriate buffers for reverse transcription, PCR, or hybridization reactions. Usually, the kit also contains instructions for carrying out the methods.

IV. Nucleic acid Vectors

Variant genes can be expressed in an expression vector in which a variant gene is operably linked to a native or other promoter. Usually, the promoter is a eukaryotic promoter for expression in a mammalian cell. The transcription regulation sequences typically include a heterologous promoter and optionally an enhancer, which is recognized by the host. The selection of an appropriate promoter, for example trp, lac, phage promoters, glycolytic enzyme promoters and tRNA promoters, depends on the host selected. Commercially available expression vectors can also be used. Suitable host cells include bacteria such as *E. coli,* yeast, filamentous fungi, insect cells, mammalian cells, typically immortalized, e.g., mouse, CHO, human and monkey cell lines and derivatives thereof. Preferred host cells are able to process the variant gene product to produce an appropriate mature polypeptide.

The invention further provides transgenic non-human animals capable of expressing an exogenous variant gene and/or having one or both alleles of an endogenous variant gene inactivated. Expression of an exogenous variant gene is usually achieved by operably linking the gene to a promoter and optionally an enhancer, and microinjecting the construct into a zygote. Inactivation of endogenous variant genes can be achieved by forming a transgene in which a cloned variant gene is inactivated by insertion of a positive selection marker. The transgene is then introduced into an embryonic stem cell, where it undergoes homologous recombination with an endogenous variant gene. Mice and other rodents are preferred animals. Such animals provide useful drug screening systems.

The invention is illustrated by the following diagrams wherein:

The following examples are given by way of illustration of the present invention and should construed to limit the scope of the present invention.

EXAMPLE 1

Identification of Allelic Variants of SCA2 Gene

This example describes the identification of allelic variants of human Spinocerebellar ataxia 2 gene by PCR and sequencing using certain oligonucleotide primers according to the invention. DNA was extracted from human peripheral blood leukocytes using a modification of the salting out procedure. The concentration of the DNA was determined by measuring the optical density of the sample, at a wavelength of 260 nm. The DNA was then amplified by polymerase chain reaction by using the oligonucleotide primers:

1. 5' CTC CGC CTC AGA CTG TTT TGG TAG 3' (as listed in SEQ ID NO: 1) and 2. 5' GTG GCC GAG GAC GAG GAG AC 3' (as listed in SEQ ID NO: 2).

The samples were denatured at 94° C. for 3 min followed by 35 cycles of denaturartion 94° C., 45 sec), annealing (52° C., 30 sec), extension (72° C., 45 sec) and a final extension of 7 min at 72° C. in a Perkin Elmer GeneAmp PCR System 9600. This reaction produced a DNA fragment of 459 bp when analysed by genescan analysis using ABI prism 377 automated DNA sequencer (459 bp product had 22 repeats at polymorphic CAG repeat region). The PCR product was purified from band cut out of agarose gel using a QIAquick gel extraction kit (Qiagen) and both the strands of the PCR product were directly sequenced using dye terminator chemistry on an ABI Prism 377 automated DNA sequencer with the PCR primers. The PCR product was shown to be identical to the human ataxin-2 (SCA2) mRNA, complete cds sequence in the data base (accession number U70323), submitted by Pulst, S. -M., except for the previously mentioned two single base changes as listed in table 1.

EXAMPLE 2

Nucleotide Sequence of the Allelic Variant of SCA2 Gene

The nucleotide sequence of the allelic variant of SCA2 gene derived using the method as described in example 1

```
5' C TCC GCC TCA GAC TGT TTT GGT AGC AAC GGC AAC GGC GGC GGC

GCG TTT CGG CCC GGC TCC CGG CGG CTC CTT GGT CTC GGC GGG CCT

CCC CGC CCC TTC GTC GTC CTC CTT CTC CCC CTC GCC AGC CCG GGC GCC

CCT CCG GCC GCG CCA ACC CGC GCC TCC CCG CTC GGC GCC CGC GCG

TCC CCG CCG CGT TCC GGC GTC TCC TTG GCG CGC CCG GCT CCC GGC
```

-continued

TGT CCC CGC CCG GCG TGC GAG CCG GTG TAT GGG CCC CTC ACC ATG

TCG CTG AAG CCC CAG CAG CAG CAG CAG CAG CAG CAG CAA CAG CAG

CAG CAG CAA CAG CAG CAG CAG CAG CAG CAG CAG CCG CCG CCC GCG

GCT GCC AAT GTC CGC AAG CCC GGC GGC AGC GGC CTT CTA GCG TCG

CCC GCC GCC GCG CCT TCG CCG TCC TCG TCC TCG GTC TCC TCG TCC TCG

GCC AC 3' (SEQ ID NO:13)

In the above sequence the two SNPs as given in Table 1 are at nucleotide position 107 and 178 respectively and are shown in bold.

EXAMPLE 3

GT Alleles are at Nearly Zero Risk for SCA2 Diseases

A method as described in example 1 is applied to a series of DNA samples extracted from Spinocerebellar ataxia 2 positive individuals and normal controls. There is observed a statistically significant difference ($p<0.0000$) in the frequency distributions of the SNP haplotypes generated using the single nucleotide polymorphisms in normal and expanded SCA2 chromosome. The results obtained are summarized in the table below:

| Diagnosis | SCA2 haplotype | |
|---|---|---|
| | GT | CC |
| Control Individuals | 70.7% | 29.3% |
| Spinocerebellar ataxia 2 Patients | 0.0% | 100.0% |

A complete association of CC haplotype with SCA2 disease chromosomes indicates that SCA2 alleles with the CC haplotype are predisposed to expansion. In other words, the absence of GT haplotype in expanded chromosomes indicates that GT alleles are at nearly zero risk for SCA2 disease. Therefore, these SNP haplotypes in the human Spinocerebellar ataxia 2 gene could be used as a method of establishing individual risk to Spinocerebellar ataxia 2. The association of the CC/GT haplotypes with the SCA2 disease was studies in an Indian population. However similar association, i.e., GT haplotype being at low risk and CC being at high risk for SCA2 disease, can be expected to hold true for other human populations also.

EXAMPLE 4

Allele Specific Primers Used for the Detection of the Allelic Variants of SCA2 Gene 1. 5' CTC GGC GGG CCT CCC CGC CCC TTC GTC GTC C 3'   (as listed in SEQ ID NO: 3)

2. 5' CTC GGC GGG CCT CCC CGC CCC TTC GTC GTC G 3'   (as listed in SEQ ID NO: 4)

3. 5' CCT CCC CGC CCC TTC GTC GTC 3'   (as listed in SEQ ID NO: 5)

4. 5' CGC CAA CCC GCG CCT CCC CGC TCG GCG CCC GC 3'   (as listed in SEQ ID NO: 6)

5. 5' CGC CAA CCC GCG CCT CCC CGC TCG GCG CCC GT 3'   (as listed in SEQ ID NO: 7)

6. 5' GCG CCT CCC CGC TCG GCG CCC G 3'   (as listed in SEQ ID NO: 8)

EXAMPLE 5

Allele Specific Oligonucleotide Probes Used for Detection of the SCA2 Gene Variants 1. 5' CCC CTT CGT CGT CCT CCT TCT CCC CCT 3'   (as listed in SEQ ID NO: 9)

2. 5' CCC CTT CGT CGT CGT CCT TCT CCC CCT 3'   (as listed in SEQ ID NO: 10)

3. 5' CGC TCG GCG CCC GCG CGT CCC CGC CGC 3'   (as listed in SEQ ID NO: 11)

4. 5' CGC TCG GCG CCC GTG CGT CCC CGC CGC 3'   (as listed in SEQ ID NO: 12)

EXAMPLE 6

Nucleic Acid Vectors Containing the SCA2 Variant Sequences

Expression vectors and host cell transformed with the allelic variant of SCA2 gene containing one or more polymorphic sites as listed in table 1, can be prepared, for example, as detailed below.

Allelic variant of SCA2 gene can be expressed in an expression vector in which the variant gene is operably linked to a native or other promoter. Usually, the promoter is a eukaryotic promoter for expression in a mammalian cell. The transcription regulation sequences typically include a heterologous promoter and optionally an enhancer, which is recognized by the host. The selection of an appropriate promoter, for example trp, lac, phage promoters, glycolytic enzyme promoters and tRNA promoters will depend on the host selected. Commercially available expression vectors can also be used.

The means of introducing the expression construct into a host cell varies will depend upon the particular construction and the target host. Suitable means include fusion, conjugation, transfection, transduction, electroporation or injection. A wide variety of host cells can be employed for expression of the variant gene, both prokaryotic and eukaryotic. Suitable host cells include bacteria such as *E. coli*, yeast, filamentous fungi, insect cells, mammalian cells, typically immortalized, e.g., mouse, CHO, human and monkey cell lines and derivatives thereof. Preferred host cells are able to process the variant gene product to produce an appropriate mature polypeptide.

ADVANTAGES

The invention shall be useful to establish genotype or base variations of SCA2 gene. The information may be useful for molecular diagnosis, prediction of an individual's disease susceptibility to SCA2, prognosis and/or the genetic analysis of SCA2 gene in a population. The frequency of these variants can also be used to predict the prevalence of SCA 2 disease among various populations.

What is claimed is:

1. A diagnostic kit for the detection of SNP haplotypes (CC/GT) comprising at least one nucleic acid consisting of a nucleic acid selected from the group consisting of SEQ ID NO: 1–12.

2. An oligonucleotide primer consisting of a sequence selected from the group consisting of:
   a) CTC CGC CTC AGA CTG TTT TGG TAG 3' (SEQ ID NO: 1); and
   b) GTG GCC GAG GAC GAG GAG AC 3' (SEQ ID NO: 2) and complements thereof.

3. A method for predicting a risk of an individual to human spinocerebellar ataxia 2 (SCA2) disease, said method comprising:
   a) amplifying genomic DNA of said individual using oligonucleotide primers to the CAG repeat-containing region of exon 1 of human SCA2 gene to obtain an amplified PCR product;
   b) identifying the nucleotides present at the polymorphic sites at nucleotides 107 and 178 of SEQ ID NO: 13; and
   c) predicting the risk of the individual to SCA2 disease based upon the haplotype present at the polymorphic sites at nucleotides 107 and 178 of SEQ ID NO:13, wherein a G at position 107 of SEQ ID NO:13 and a T at position 178 of SEQ ID NO: 13 haplotype is indicative of a lower risk of SCA2 disease, and wherein a C at position 107 of SEQ ID NO:13 and a C at position 178 of SEQ ID NO:13 haplotype is indicative of an increased risk for SCA2 disease.

4. The method as claimed in claim 3 wherein the primers are selected from the group consisting of:
   a) CTC CGC CTC AGA CTG TTT TGG TAG 3' (SEQ ID NO:1);
   b) GTG GCC GAG GAC GAG GAG AC 3' (SEQ ID NO:2); and complements thereof.

* * * * *